| United States Patent [19] | [11] 4,169,931 |
|---|---|
| Rottmaier et al. | [45] Oct. 2, 1979 |

[54] PROCESS FOR THE PREPARATION OF (THIO)HYDANTOINS SUBSTITUTED WITH AMIDE GROUPS

[75] Inventors: Ludwig Rottmaier; Rudolf Merten, both of Leverkusen, Fed. Rep. of Germany

[73] Assignee: Bayer Aktiengesellschaft, Fed. Rep. of Germany

[21] Appl. No.: 897,683

[22] Filed: Apr. 19, 1978

[30] Foreign Application Priority Data

Apr. 22, 1977 [DE] Fed. Rep. of Germany ....... 2718101

[51] Int. Cl.$^2$ .............................................. C08G 18/00
[52] U.S. Cl. ....................................... 528/49; 528/68; 528/75; 548/310; 548/313
[58] Field of Search ............................ 528/68, 49, 75; 548/310, 313

[56] References Cited

U.S. PATENT DOCUMENTS

| 3,549,599 | 12/1970 | Merten | 528/68 |
| 4,089,860 | 5/1978 | Merten et al. | 548/310 |

*Primary Examiner*—Maurice J. Welsh
*Attorney, Agent, or Firm*—Connolly and Hutz

[57] ABSTRACT

A process for the preparation of an amide-substituted (thio)hydantoin which comprises reacting a primary mono- or poly-amine with an optionally substituted maleic acid amide reacting the resulting product with an organic mono- or poly-iso(thio)cyanate and subsequently cyclizing the resulting product by the action of heat.

18 Claims, No Drawings

PROCESS FOR THE PREPARATION OF (THIO)HYDANTOINS SUBSTITUTED WITH AMIDE GROUPS

The preparation of hydrantoins modified by amide groups is known. They are prepared by reacting aspartic acid esters with isocyanates or isothiocyanates, cyclising the thus-obtained reaction products to give hydantoin-5-acetic acid esters and reacting the resulting esters with amines, the reaction being accompanied by the elimination of alcohols.

It has now been found that hydantoins substituted with amide groups, preferably in the 5-position, may be obtained easily and in very good yields by reacting amines with optionally substituted maleic amide acids optionally prepared in situ, reacting the aspartic amide acids formed with organic isocyanates or isothiocyanates and cyclising the thus-obtained reaction products under the effect of heat and catalysts.

Accordingly, the present invention relates to a process for the preparation of (thio)hydantoins substituted by amide groups, wherein optionally substituted maleic acid mono amides corresponding to the following general formula (I):

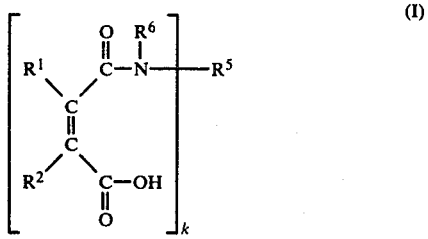

wherein
$R_1$, $R_2$ and $R_6$, which may be the same or different, each represents hydrogen or an aliphatic radical;
$R_5$ represents hydrogen or an optionally substituted aliphatic, cycloaliphatic, aromatic, aliphatic-aromatic or heterocyclic radical; and
k represents an integer of from 1 to 3, preferably 1 or 2;
are reacted with a primary monoamine or polyamine, the reaction product is reacted with an organic mono- or polyiso(thio) cyanate and the product of this reaction is cyclised by subsequent heating, optionally in the presence of catalysts.

The term "(thio)hydantoins" as used herein including the claims is intended to mean a compound selected from the group consisting of hydantoins and thiohydantoins. Similarly, the term "iso(thio)cyanate" is intended to mean a compound selected from the group consisting of isocyanate and thiocyanate.

Preferred maleic acid mono amides suitable for the process according to the present invention are acid mono amides corresponding to general formula (I) wherein
$R_1$, $R_2$ and $R_6$, which may be the same or different, each represents hydrogen or a $C_1$-$C_{18}$ alkyl radical which may optionally be substituted by halogen, such as chlorine or bromine; and
$R_5$ represents hydrogen, a $C_1$-$C_{20}$ alkyl radical, a $C_5$-$C_{12}$ cycloalkyl radical which both may optionally be substituted by halogen (preferably chlorine or bromine), by a hydroxy, $C_1$-$C_{18}$ alkoxy, $C_2$-$C_{18}$ alkoxy carbonyl group or by a hydroxy carbonyl group, a $C_6$-$C_{16}$ aryl radical which may optionally by substituted by halogen (preferably chlorine or bromine), nitro group, $C_1$-$C_{18}$ alkyl, $C_1$-$C_{18}$ haloalkyl, hydroxy, $C_1$-$C_{18}$ hydroxyalkoxy, $C_1$-$C_{18}$ hydroxyalkoxy, $C_2$-$C_{18}$ alkoxy carbonyl or hydroxy carbonyl groups, a $C_7$-$C_{18}$ aralkyl radical or a $C_5$-$C_{12}$ heterocyclic radical containing one or more N, O and/or S-atoms in the ring. Heterocyclic radicals are preferably aromatic or cycloaliphatic 5- or 6-membered rings which contain one or more oxygen, nitrogen and/or sulphur atoms, for example radicals derived from furan, pyridine, thiophene, imidazole, pyrimidine and piperazine. With particular preference, $R_5$ represents hydrogen a $C_1$-$C_8$ alkyl radical, a $C_6$-$C_{16}$ aryl radical, such as phenyl, naphthyl, bisphenyl or diphenyl radicals attached through O, S, $SO_2$, $CH_2$, $CH_3$—C-$CH_3$ or CO.

Amide acids of maleic acids, such as maleic acid mono amide, N-methyl-, N-butyl-, N-phenyl maleic acid mono amide, bis-maleic acid mono amide based on hexamethylene diamine, diaminodiphenyl methane, phenylene diamine, tolylene diamine and naphthylene diamine are especially preferred.

Such maleic acid mono amides are produced by reacting maleic acid anhydride with the corresponding monoamines or polyamines, as adequately described in the literature.

The monoamines or polyamines used for the reaction according to the present invention preferably correspond to the following general formula:

wherein
$R^3$ has the same meaning as $R^5$, except for hydrogen; and
l represents an interger of from 1 to 3, preferably 1 or 2.

$R^3$ is derived with particular preference from a $C_1$-$C_{18}$ alkyl radical, $C_5$ or $C_6$ cycloalkyl radical or a $C_1$-$C_{16}$ aryl radical optionally substituted by halogen, $C_1$-$C_3$ alkyl or $C_1$-$C_3$ alkoxy groups, such as phenyl, naphthyl, bisphenyl, benzyl or diphenyl radicals attached through O, S, $SO_2$, $CH_2$, $CH_3$—C—$CH_3$ or CO. Primary amines which are especially preferred for the process according to the present invention include: methylamine, ethylamine, butylamine, cyclohexylamine, ethylene diamine, propylene diamine, tetramethylene diamine, hexamethylene diamine, technical mixtures of trimethyl hexamethylene diamine, 1,4-diaminocyclohexane, 1-aminomethyl-5-amino-1,3,3-trimethyl cyclohexane (isophorone diamine), 4,4'-diaminodicyclohexylmethane, ethanol diamine, propanol amine, isopropanolamine, aniline, aminophenol, 3- and 4-aminobenzoic acid or its esters, benzylamine, m- and p-phenylene diamine, 2,4- and 2,6-diaminotoluene or commercial mixtures thereof, m- and p-xlylene diamine or commercial mixtures thereof, 1,5-naphthylene diamine, benzidine, 4,4'-diaminodiphenyl methane and its technical isomer mixtures, 2,2-bis-(4-aminophenyl-propane and 4,4'-diaminodiphenyl ether.

In the context of the present invention, mono(thio)isocyanates are aliphatic and aromatic compounds optionally substituted by hetero atoms and containing an NCO-group in the molecule, for example alkyl isocyanates, such as ethyl, methyl, butyl, dodecyl and stearyl isocyanate, aromatic, optionally substituted monoisocyanates, such as phenyl, tolyl, isopropyl, nonyl-chloro, tetrachloro, pentachloro, benzyl, bromophenyl isocyanate or isocyanatobenzoic acid esters, phthalic acid esters, isophthalic acid esters, isocyanatobenzonitrile, cycloaliphatic isocyanates, such as cyclohexyl isocyanate, and unsaturated isocyanates, such as allyl, oleyl and cyclohexenyl isocyanate.

Other starting components suitable for use in accordance with the present invention are aliphatic, cycloaliphatic, araliphatic, aromatic and heterocyclic polyisocyanates, preferably diisocyanates (cf. Annalen 562, pages 75 to 136), for example ethylene diisocyanate, 1,4-tetramethylene diisocyanate, 1,6-hexamethylene diisocyanate, 1,12-dodecane diisocyanate, cyclobutane-1,3-diisocyanate, cyclohexane-1,3- and -1,4-diisocyanate and mixtures of these isomers, 1-isocyanato-3,3,5-trimethyl-5-isocyanatomethyl cyclohexane (DAS No. 1,202,785), 2,4- and 2,6-hexahydrotolylene diisocyanate and mixtures of these isomers, hexahydro-1,3- and/or -1,4-phenylene diisocyanate, perhydro-2,4'- and/or -4,4'-diphenyl methane diisocyanate, 1,3- and 1,4-phenylene diisocyanate, 2,4- and 2,6-tolylene diisocyanate and mixtures of these isomers, diphenyl methane-2,4'- and/or -4,4'-diisocyanate, naphthylene-1,5-diisocyanate, triphenyl methane-4,4',4''-triisocyanate, polyphenyl-polymethylene-polyisocyanates of the type obtained by condensing aniline with formaldehyde, followed by phosgenation, and described, for example, in British Pat. Nos. 874,430 and 848,671, perchlorinated aryl polyisocyanates of the type described, for example, in German Auslegeschrift No. 1,157,601, polyisocyanates containing carbodiimide groups of the type described in German Pat. No. 1,092,007, diisocyanates of the type described in U.S. Pat. No. 3,492,330, polyisocyanates containing allophanate groups of the type described, for example, in British Pat. No. 994,890, in Belgian Pat. No. 761,626 and in Published Dutch Pat. application No. 7,102,524, polyisocyanates containing isocyanurate groups of the type described, for example, in German Pat. Nos. 1,022,789; 1,222,067 and 1,027,394 and in German Offenlegungsschrift Nos. 1,929,034 and 2,044,048, polyisocyanates containing urethane groups of the type described, for example, in Belgian Pat. No. 752,261 or in U.S. Pat. No. 3,394,164, polyisocyanates containing acylated urea groups according to German Pat. No. 1,230,778, polyisocyanates containing biuret groups of the type described, for example, in German Pat. No. 1,101,394, in British Pat. No. 889,050 and in French Pat. No. 7,017,514, polyisocyanates produced by telomerisation reactions of the type described, for example, in Belgian Pat. No. 723,640, polyisocyanates containing ester groups of the type described for example, in British Pat. Nos. 956,474 and 1,072,956, in U.S. Pat. No. 3,567,763 and in German Patent No. 1,231,688, reaction products of the above-mentioned isocyanates with acetylene according to German Pat. No. 1,072,358.

It is also possible to use the distillation residues containing isocyanate groups of the type obtained in the commercial production of isocyanates, optionally in solution in one or more of the above-mentioned polyisocyanates.

Preferred mono- and poly-iso(thio) cyanates correspond to the following general formulae:

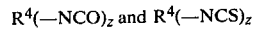

wherein $R^4$ has the same meaning as $R^5$, except for hydrogen and excluding the substituents hydroxy, hydroxyalkoxy or hydroxy carbonyl; and z represents an integer of from 1 to 3, preferably 1 or 2.

$R^4$ preferably represents an aliphatic $C_1$-$C_{20}$ radical which may optionally be substituted by halogen, $C_1$-$C_6$ alkyl and/or $C_6$-$C_{16}$ aryl groups, a $C_6$-$C_{16}$ aromatic radical, a $C_5$-$C_{12}$ cycloaliphatic radical, a $C_7$-$C_{20}$ aliphatic-aromatic radical and a $C_5$-$C_{12}$ aromatic or cycloaliphatic radical containing hetero atoms, such as N, O or S. Especially preferred $R_5$ represents a $C_2$-$C_{12}$ aliphatic radical or a $C_6$-$C_{16}$ aryl radical, such as phenyl, tolyl, naphthyl, diphenyl methane, diphenyl ether, bisphenyl or diphenyl radicals attached through S, $SO_2$—CO or $CH_3$—C—$CH_3$.

It is particularly preferred to use the commercially readily obtainable mixtures of tolylene diisocyanates, m-phenylene diisocyanate, phenylisocyanate and its substitution products, also phosgenated condensates of aniline and formaldehyde with a polyphenylene-methylene structure and the symmetrical compounds 4,4-diisocyanatodiphenyl methane, 4,4'-diisocyanatodiphenyl ether, p-phenylene diisocyanate, 4,4'-diisocyanatodiphenyl dimethyl methane, analogous hydroaromatic diisocyanates and also aliphatic diisocyanates containing from 2 to 12 carbon atoms, such as hexamethylene diisocyanate and diisocyanates derived from isophorone.

The isocyanates may be used in free form and also partly or completely in the form of the derivatives thereof obtainable by reaction with compounds containing reactive hydrogen and reacting as donors under the reaction conditions.

The donors preferably used are the acyl ureas obtainable from lactams, for example caprolactam, and the carbamic acid esters obtained from aromatic and aliphatic monohydroxy and polyhydroxy compounds which correspond for example, to the following general formulae:

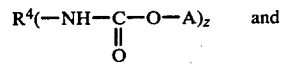

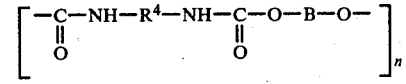

wherein $R^4$ and z are as defined above; and A represents the organic radical of a monohydroxy compound; and B the organic radical of a bis-functional or tris-functional hydroxy compound, preferably both, the same or different, an aliphatic $C_1$-$C_{10}$ radical, a cycloaliphatic $C_5$-$C_{10}$ radical, an aliphatic-aromatic $C_7$-$C_{12}$ radical and an aromatic $C_6$-$C_{12}$ radical which, in each case, may also be substituted by $C_1$-$C_8$ alkyl and/or $C_6$-$C_{12}$ aryl groups; and n represents an integer of from 1 to 1000, preferably from 1 to 100.

Examples include: the carbamic acid esters of phenol, isomeric cresols, technical mixtures thereof and similar aromatic hydroxyl compounds, aliphatic monohydric alcohols, such as methanol, ethanol, propanol, isopropanol, butanol, isobutanol, diethylene glycol monomethyl ether, cyclohexanol, and benzyl alcohol, and aliphatic diols or polyols, such as ethylene glycol and trimethylol propane.

The urethanes may be used as such or may initially be produced in situ by reaction with alcohols.

Instead of using the above mentioned mono- and (poly)isocyanates, it is also possible to use the corresponding (poly)isothiocyanates.

The process according to the present invention may be reproduced by the following equation:

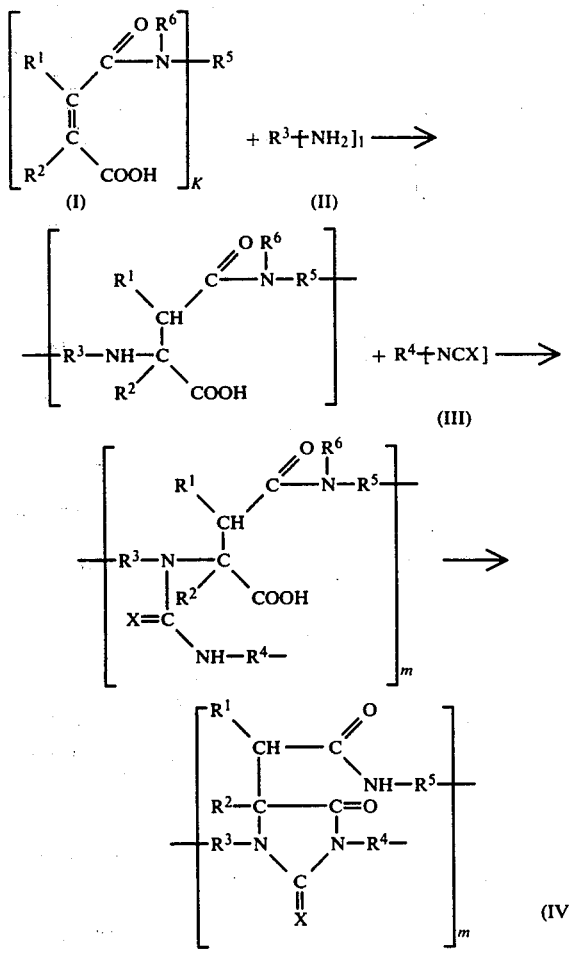

wherein $R_1$ to $R_6$ are as defined above; and when k, l and z=1 a monomolecular compound is formed and, when k and/or l and/or z>1, a higher molecular compound is formed, the hydantoin rings being attached through the radicals $R_5$ and/or $R_3$ and/or $R_4$; and m represents an integer from 1 to 1000, preferably from 1 to 100.

The reaction between the maleic acid amides and the amines generally takes place at temperatures of from $-20°$ to $+200°$ C., preferably optionally in inert solvents and optionally in the presence of an effective quantity of an acid catalyst. The acid catalyst may also be used as solvent. Suitable acid catalysts are carboxylic acids, such as acetic acid, butyric acid, pivalic acid, benzoic acid or trichloroacetic acid, phenols, cresols and phenols acidified by electrophilic substitution.

Where $R_3$ and $R_5$ are identical, these aminoaspartic acid amides used in accordance with the present invention may be directly obtained from maleic acid anhydrides and the corresponding amines.

The reaction between the aminoaspartic acid amides and the iso(thio)cyanates generally takes place at temperatures of from $-20°$ to $+120°$ C., and preferably from $0°$ to $80°$ C., optionally in inert solvents and optionally in the presence of the catalysts normally used for amine-iso(thio)cyanate addition reactions.

Preferred inert solvents ae aliphatic or aromatic hydrocarbons and the halogenation products thereof, such as diisopropyl benzene, methyl naphthalene, di- or trichlorobenzene, or polar solvents, such as N-methyl pyrrolidone, dimethyl formamide, dimethyl acetamide, phenol, cresols or xylenols.

Cyclisation to form the hydantoins substituted by amide groups may be carried out in the presence of the catalysts normally used in the production of hydantoins, preferably triethylamine, dimethyl aniline, "Dabco", acetic acid, pivalic acid, benzoic acid, or metal catalysts, such as $BF_3$, titanium tetrabutylate or iron acetyl acetonate, at temperatures of from $120°$ to $250°$ C., and preferably from $150°$ to $200°$ C. Reaction times of from 1 to 10 hours are generally necessary.

The reaction components are generally used in stoichiometric quantities. However, it is also possible that one of the components is used in excess in order to obtain polymers containing further reactive groups. The reaction products are worked up in the conventional way, for example by distillation or crystallisation processes. Polymeric products may be directly solved on metal sheets or wires in known manner to produce lacquers. However, they may also be obtained in pure form by percipitation, for example with acetone or methanol, and thus further processed into films, for example.

The hydantoins modified by amide groups which are obtained in accordance with the present invention may be incorporated by way of an amide group and, optionally, in the presence of further reactive groups on the radicals $R_3$, $R_4$ and $R_5$, into a variety of different polymers for increasing the thermal resistance thereof, for example by reaction with mono- or poly-carboxylic acids and derivatives thereof or with monohydric alcohols or polyhydric alcohols to form polyesters having increased thermal stability.

The monohydantoins may be used as plant protection agents or as pharmaceutical products.

The polyhydantoins according to the present invention are distinguished by the particular thermal stability thereof and are suitable for use as adhesives, lacquers, films shaped articles. The properties thereof may be varied within wide limits for a variety of different applications by the addition of fillers, pigments and low and high molecular weight components, for example for the production of lacquers and films by blending with polyesters or polyamides.

EXAMPLE 1:

1-cyclohexyl-3-phenyl-5-(phenylaminocarbonylmethylene)-hydantoin 95.5 parts of the compound:

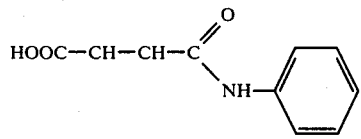

are suspended in 300 parts of cresol, followed by the addition, at from 30° to 40° C., of 49.5 parts of cyclohexylamine. The solution formed is left standing overnight, after which 59.5 parts of phenyl isocyanate are added at from 15° to 20° C. After stirring for 2 hours at room temperature, 0.2 part of 1,4-diazabicyclo(2,2,2)octane [=Dabco ®] are added, after which the mixture is heated to 165° C. and stirred for 3 hours at that temperature. The solvent is distilled off and the oily residue dissolved in 150 parts of hot ethanol, 117 parts of the assumed compound melting at 198° C. crystallise out on cooling. IR- and NMR-spectra confirm the assumed structure.

Analysis: calculated: 70.6% C; 6.5% H and 10.7% N; observed: 70.7% C; 6.45% H and 10.8% N.

EXAMPLE 2:

1,3-diphenyl-5-(phenylaminocarbonyl-methylene)-hydantoin 95.5 parts of the compound:

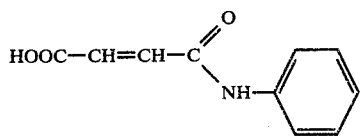

are suspended in 300 parts of cresol, after which 46.5 parts of aniline are added at 80° C. and the mixture stirred for 30 minutes at 100° C. On the following day, 59.5 parts of phenyl isocyanate are added dropwise at from 30° to 40° C., after which the mixture is stirred for 30 minutes at room temperature, 0.1 part of Dabco ® is added, the mixture heated to 165° C. and then maintained for 4 hours at that temperature. The solvent is distilled off in vacuo and the oily residue is dissolved in 150 parts of ethanol. The deposit formed on cooling is filtered off under suction, washed with ethanol and dried (m.p.=214° C., after recrystallisation from ethanol m.p.=219° C.). NMR- and IR-spectra confirm the assumed structure.

Analysis: calculated: 71.6% C; 4.9% H and 10.9% N; observed: 71.7% C; 5.1% H and 10.9% N.

EXAMPLE 3:

1-cyclohexyl-3-(2-chloro)-phenyl-5-(2-chlorophenyl-aminocarbonyl-methylene)-hydantoin 85 parts of the compound:

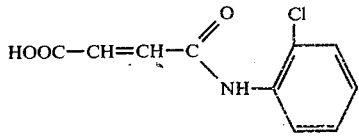

are suspended in 300 parts of cresol, after which 37.3 parts of cyclohexylamine are added at 10° C. and the mixture left standing overnight at room temperature. 54.2 parts of 2-chlorophenyl isocyanate are then added dropwise at 10° C., after which the mixture is stirred for 1.5 hours, 0.1 part of Dabco ® is added and the reaction mixture stirred for another 5 hours at 180° C. After the solvent has been distilled off, 150 parts of ethanol are added, the hot solution is filtered and petroleum ether is added to the mother liquor. The deposit formed is filtered off under suction, washed and dried (m.p.=197° C.). NMR- and IR-spectra confirm the assumed structure.

Analysis: calculated: 60.0% C; 5.0% H; 9.1% N and 15.4% Cl; observed: 59.9% C; 5.0% H; 9.0% N and 15.2% Cl.

EXAMPLE 4

95.5 parts of the compound

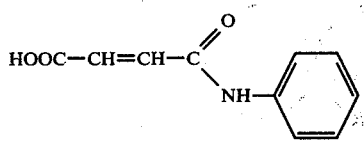

are suspended in 464 parts of cresol followed by the dropwise addition at 100° C. of 49.5 parts of 4,4'-diaminodiphenyl urethane dissolved in 100 parts of toluene. The solution is stirred for 20 hours at 100° C. 62.5 parts of 4,4'-diisocyanato-diphenyl urethane dissolved in 100 parts of toluene are then added dropwise at 0° C. after which the mixture is stirred for 2.5 hours with gradual heating to room temperature. After the addition of 0.1 part of Dabco ® the mixture is heated to 160° C. and stirred for 6 hours at that temperature.

662 parts of 30% polyhydantoin solution are obtained. After dilution to 15%, this polyhydantoin solution has a viscosity (at 25° C.) of 333 cP. According to the IR-spectrum (characteristic bands for hydantoin at 1775 and 1720 cm$^{-1}$ and for amide at 1690 cm$^{-1}$), the compound obtained is the assumed compound containing the recurring structural unit shown below. A lacquer film stoved on sheet metal shows good elasticity combined with extremely good thermal properties.

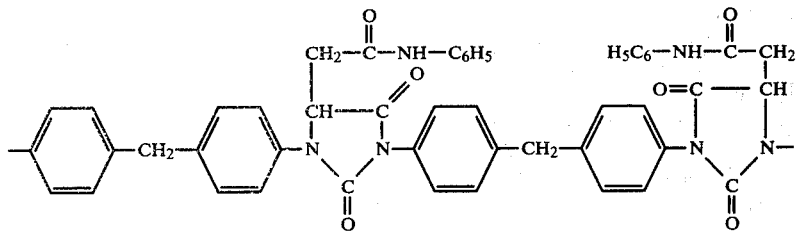

EXAMPLE 5

95.5 parts of the compound

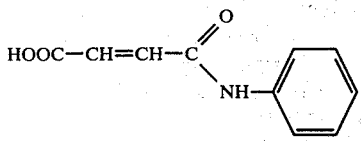

are suspended in 415 parts of cresol, followed by the dropwise addition at 10° C., of 29 parts of hexamethylene diamine dissolved in 100 parts of toluene. The solution formed is left standing overnight. 62.5 parts of 4,4'-di-isocyanatodiphenyl methane dissolved in 100 parts of toluene are then added dropwise at 0° C., after which the mixture is stirred for 2.5 hours with gradual heating to room temperature. After the addition of 0.1 part of Dabco ®, the mixture is heated to 160° C. and stirred for 6 hours at that temperature. 596 parts of a 30% polyhydantoin solution are obtained. After dilution to 15%, this polyhydantoin solution has a vicosity (at 25° C.) of 665 cP. According to the IR-spectrum (characteristic bands for hydantoin at 1775 and 1720 cm$^{-1}$ and for amide at 1690 cm$^{-1}$), the compound obtained is the assumed compound containing the recurring structural unit shown below. A lacquer film stoved on sheet metal shows good elasticity combined with extremely good thermal properties.

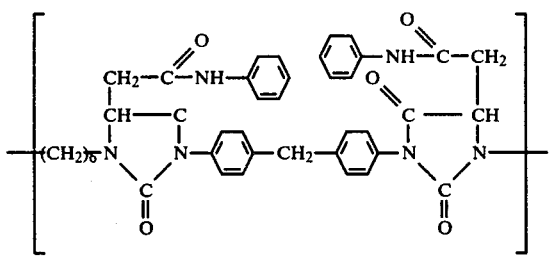

What we claim is:

1. Processes for the preparation of amide-substituted (thio)hydantoins which comprises reacting a primary mono- or poly-amine with a maleic acid amide corresponding to the following general formula (I):

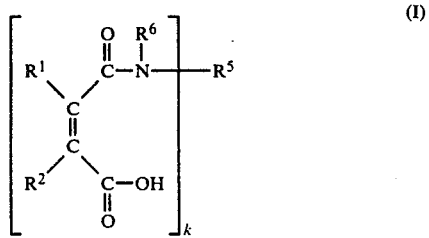

wherein $R_1$, $R_2$ and $R_6$, which may be the same or different, each represents hydrogen or an optionally substituted aliphatic radical;

$R_5$ represents hydrogen or an optionally substituted aliphatic, cycloaliphatic, aromatic, aliphatic-aromatic or heterocyclic radical; and k represents an integer of from 1 to 3; reacting the resulting product with an organic mono- or poly-iso(thio)cyanate and subsequently cyclising the resulting product by the action of heat.

2. Processes as claimed in claim 1 in which, in general formula (I), $R_1$, $R_2$ and $R_6$ represents hydrogen or a $C_1$–$C_{18}$ alkyl radical optionally substituted by halogen, $R_5$ represents hydrogen, a $C_1$–$C_{20}$ alkyl radical, a $C_5$–$C_{12}$ cycloalkyl radical which both may optionally be substituted by halogen, by a hydroxy, by $C_1$–$C_{18}$ alkoxy, by $C_2$–$C_{18}$ alkoxy carbonyl group or by a hydroxy carbonyl group, a $C_6$–$C_{16}$ aryl radical which may optionally be substituted by halogen, nitro group by $C_1$–$C_{18}$ alkyl, by $C_1$–$C_{18}$ haloalkyl, hydroxy, by $C_1$–$C_{18}$ hydroxyalkoxy, by $C_2$–$C_{18}$ alkoxy carbonyl or by hydroxy carbonyl groups, a $C_7$–$C_{18}$ aralkyl radical or a $C_5$–$C_{12}$ heterocyclic radical containing N, O and/or S-atoms in the ring, and k represents 1 or 2.

3. Processes as claimed in claim 2, wherein $R_5$ represents hydrogen, a $C_1$–$C_8$ alkyl radical or a $C_6$–$C_{16}$ aryl radical.

4. Processes as claimed in claim 1, wherein the maleic acid amides are maleic acid mono amide, N-methyl, N-butyl, N-phenyl maleic acid mono amide, bis-amide acid mono amide based on hexamethylene diamine, diaminodiphenyl methane, phenylene diamine, tolylene diamine or naphthylene diamine.

5. Processes as claimed in claim 1 wherein the cyclisation is carried out in the presence of a catalyst.

6. Processes as claimed in claim 1 wherein the primary mono- or polyamine corresponds to the following general formula (III):

wherein $R^3$ represents an optionally substituted aliphatic, cycloaliphatic, aromatic, aliphatic-aromatic or heterocyclic radical; and l represents an integer of from 1 to 3.

7. Processes as claimed in claim 6 in which, in general formula (II), l represents 1 or 2, $R_3$ has the meaning of $R_5$, except for hydrogen.

8. Processes as claimed in claim 7, wherein $R_3$ represents a $C_1$–$C_{18}$ alkyl radical, $C_5$ or $C_6$ cycloalkyl radical or a $C_1$–$C_{16}$ aryl radical optionally substituted by halogen, by $C_1$–$C_3$ alkyl or by $C_1$–$C_3$ alkoxy groups.

9. Processes as claimed in claim 1 wherein the mono- or poly-iso(thio)cyanate corresponds to one of the following general formulae (III):

wherein $R_4$ represents an optionally substituted aliphatic, cycloaliphatic, aromatic, aliphatic-aromatic or heterocyclic radical, excluding the substituent hydroxy, hydroxyalkoxy and hydroxy carbonyl; and z represents an integer of from 1 to 3.

10. Processes as claimed in claim 9 wherein in general formulae (III), z represents 1 or 2, and $R^4$ has the meaning of $R^5$.

11. Processes as claimed in claim 9, wherein $R_4$ represents an aliphatic $C_1$–$C_{20}$ radical which may optionally be substituted by halogen, by $C_1$–$C_6$ alkyl and/or by $C_6$–$C_{16}$ aryl groups, a $C_6$–$C_{16}$ aromatic radical, a $C_5$–$C_{12}$ cycloaliphatic radical, a $C_7$–$C_{20}$ aliphatic-aromatic radical or a $C_5$–$C_{12}$ aromatic or cycloaliphatic radical containing a hetero atom in the ring thereof.

12. Processes as claimed in claim 1 wherein the reaction between the amine and the acid amide is carried out at a temperature of from −20° to +200° C.

13. Processes as claimed in claim 1 wherein the reaction of the iso(thio)cyanate is carried out at a temperature of from −20° to +120° C.

14. Processes as claimed in claim 13 wherein the said temperature is from 0° to 80° C.

15. Processes as claimed in claim 1 wherein cyclisation is carried out at a temperature of from 120° to 250° C.

16. Processes as claimed in claim 15 wherein the said temperature is from 150° to 200° C.

17. An amide-substituted (thio) hydantoin when prepared by a process as claimed in claim 1.

18. A lacquer composition comprising an amide-substituted (thio) hydantoin as claimed in claim 17.

* * * * *